United States Patent
Tessier et al.

(10) Patent No.: US 10,894,082 B2
(45) Date of Patent: Jan. 19, 2021

(54) ANTI-S100A8 FOR TREATING LEUKEMIA

(71) Applicant: UNIVERSITÉ LAVAL, Québec (CA)

(72) Inventors: Philippe Tessier, Montréal (CA);
Malika Laouedj, Québec (CA);
Frédéric Barabe, Québec (CA);
Natalie Pagé, Québec (CA)

(73) Assignee: UNIVERSITÉ LAVAL, Québec, QC (CA)

( * ) Notice: Subject to any disclaimer, the term of this patent is extended or adjusted under 35 U.S.C. 154(b) by 151 days.

(21) Appl. No.: 15/759,362

(22) PCT Filed: Sep. 13, 2016

(86) PCT No.: PCT/CA2016/051078
§ 371 (c)(1),
(2) Date: Mar. 12, 2018

(87) PCT Pub. No.: WO2017/045070
PCT Pub. Date: Mar. 23, 2017

(65) Prior Publication Data
US 2018/0256710 A1 Sep. 13, 2018

Related U.S. Application Data

(60) Provisional application No. 62/259,738, filed on Nov. 25, 2015, provisional application No. 62/218,000, filed on Sep. 14, 2015.

(51) Int. Cl.
| A61K 39/00 | (2006.01) |
| A61K 39/395 | (2006.01) |
| C07K 16/24 | (2006.01) |
| A61P 35/02 | (2006.01) |
| C07K 16/18 | (2006.01) |
| A61K 31/351 | (2006.01) |
| A61K 31/513 | (2006.01) |

(52) U.S. Cl.
CPC ........ *A61K 39/3955* (2013.01); *A61K 39/395* (2013.01); *A61P 35/02* (2018.01); *C07K 16/18* (2013.01); *C07K 16/24* (2013.01); *A61K 31/351* (2013.01); *A61K 31/513* (2013.01); *A61K 2039/505* (2013.01); *A61K 2300/00* (2013.01)

(58) Field of Classification Search
CPC .................................................. A61K 39/3955
See application file for complete search history.

(56) References Cited

U.S. PATENT DOCUMENTS

2007/0231317 A1* 10/2007 Tessier ............... A61K 31/7105
424/130.1
2010/0316655 A1* 12/2010 Hall ..................... A61K 31/404
424/174.1

FOREIGN PATENT DOCUMENTS

| WO | 2004/004770 | 1/2004 |
| WO | 2006005186 | 1/2006 |

OTHER PUBLICATIONS

Barabe et al., "Myeloid-related protein S100A9 induces cellular differentiation in acute myeloid leukemia through TLR2 and TLR4 receptors". Blood, Dec. 2015, vol. 126, No. 23, pp. 3858.
Spijkers-Hagelstein, et al., "Elevated S100A8/S100A9 espression causes glucocorticoid resistance in MLL-rearranged infant acute lymphoblastic leukemia". Leukemia, Jun. 2012, vol. 26, No. 6, pp. 1255-1265.
Yang L. et al., "S100A8-targeting siRNA enhances arsenic trioxide-induced myeloid leukemia cell death by down-regulating autophagy". Int. J. Mol. Med., Jan. 2012, vol. 29, No. 1, pp. 65-72.
Yang M. et al., "S100A8 contirbutes to drug resistance by promoting autophagy in leukemia cells". PLoS one, May 2014, vol. 9, No. 5.
Laouedj et al. "S100A9 induces differentiation of acute myeloid leukemia cells through TLR4", Blood, 2017, vol. 129, No. 14.

* cited by examiner

*Primary Examiner* — Sheela J. Huff
(74) *Attorney, Agent, or Firm* — Norton Rose Fulbright

(57) ABSTRACT

The present description relates to an anti-S1008 protein for treating leukemia. More specifically, is disclosed anti-S100A8 antibody that specifically binds to a portion of S100A8 protein and/or a S100A8/S100A9 heterodimer for treating leukemia.

14 Claims, 5 Drawing Sheets

Specification includes a Sequence Listing.

ANTI-S100A8 FOR TREATING LEUKEMIA

CROSS-REFERENCE TO RELATED APPLICATIONS

This application is a U.S. National Phase of International Application No. PCT/CA2016/051078, filed on Sep. 13, 2016 and claiming priority from U.S. provisional patent applications 62/218,000 filed Sep. 14, 2015, and 62/259,738 filed Nov. 25, 2015 and this application claims priority to and the benefit of the above-identified applications, each of which are incorporated by reference herewith in their entirety.

TECHNICAL FIELD

The present description relates to an anti-S1008 protein for treating leukemia.

BACKGROUND ART

Acute leukemias are the result of a series of genetic and epigenetic events occurring in a stem or progenitor hematopoietic cell, giving rise to a clonal expansion of progenitors with an impaired capacity to differentiate. The past 20 years have been very fruitful in the identification of recurrent genetic lesions in acute leukemia. Improvement in leukemia-free survival has been mostly due to better risk stratification which allows for adjustment of treatment intensity and also to allogenic hematopoietic stem cell transplantation. However, drugs used in acute myeloid treatment (AML) are basically the same today as they were 25-30 years ago and prognosis remains poor. The 5-year survival rate is as low as 55% for children with AML and even worse for adults (30-40%) and elderly (>65 yo) (<15%). Therefore, novel and innovative approaches need to be explored in order to improve leukemia-free survival of acute leukemia patients.

There is thus still a need to be provided with a composition or methodology for treating leukemia.

SUMMARY

In accordance with the present invention there is now provided an anti-S100A8 for treating leukemia.

In an embodiment, the anti-S100A8 is an antibody.

In another embodiment, the anti-S100A8 specifically binds to a portion of S100A8 protein.

In a further embodiment, the anti-S100A8 specifically binds to a S100A8/S100A8 homodimer or a S100A8/S100A9 heterodimer.

In an additional embodiment, the S100A8 protein is a human S100A8.

In another embodiment, the human S100A8 comprises the amino acid sequence depicted in SEQ ID NO: 1.

In a further embodiment, the anti-S100A8 is monoclonal or polyclonal antibody.

In an embodiment, the anti-S100A8 is a mouse antibody, a goat antibody, a human antibody or a rabbit antibody.

In another embodiment, the anti-S100A8 is a humanized antibody.

In an embodiment, the anti-S100A8 antibody comprises an epitope binding fragment selected from the group consisting of: Fv, F(ab'), or F(ab')2.

In another embodiment, the anti-S100A8 antibody comprises a heavy chain variable region encoded by the nucleotide sequence set forth in SEQ ID NO: 3.

In a supplemental embodiment, the anti-S100A8 antibody comprises a heavy chain variable region consisting of SEQ ID NO: 4.

In another embodiment, the anti-S100A8 antibody comprises a light chain variable region encoded by the nucleotide sequence set forth in SEQ ID NO: 5.

In another embodiment, the anti-S100A8 antibody comprises a light chain variable region consisting of SEQ ID NO: 6.

In another embodiment, the anti-S100A8 is formulated for an injection.

In another embodiment, the anti-S100A8 is formulated for an administration with a chemotherapeutic agent.

In an embodiment, the chemotherapeutic agent is at least one of daunorubicin, doxorubicin and cytarabine.

In another embodiment, the anti-S100A8 is formulated for a simultaneous or separate administration with the chemotherapeutic agent.

In a further embodiment, the anti-S100A8 is formulated for an administration after a chemotherapeutic treatment to a subject.

It is also provided herein a composition comprising the anti-S100A8 as described herein and a carrier.

In an embodiment, the composition described herein is for the treatment of leukemia.

In an embodiment, the leukemia is acute lymphoblastic leukemia (ALL), acute myeloid leukemia (AML), chronic lymphocytic leukemia (CLL), chronic myeloid leukemia (CML) and chronic myelomonocytic leukemia (CMML).

In an embodiment, the composition described herein is for stimulating cell differentiation.

In an embodiment, the composition described herein is for inhibiting cell proliferation.

In an embodiment, the composition described herein is for the treatment of acute myeloid leukemia (AML).

It is also provided a method of treating leukemia in a subject comprising the step of administering the anti-S100A8 or the composition described herein to the subject.

It is also provided a method of stimulating cell differentiation in a subject comprising the step of administering the anti-S100A8 or the composition described herein to the subject.

It is also provided a method for inhibiting cell proliferation in a subject comprising the step of administering the anti-S100A8 or the composition described herein to the subject.

It is also provided a method of stimulating cell differentiation ex vivo comprising the step of administering the anti-S100A8 or the composition described herein to the subject.

It is further provided a method for inhibiting cell proliferation ex vivo comprising a step of administering the anti-S100A8 or the composition described herein to the subject.

It is additionally provided the use of the anti-S100A8 or the composition described herein for treating leukemia in a subject.

It is also provided the use of the anti-S100A8 or the composition described herein in the manufacture of a medicament for treating leukemia in a subject.

It is also provided the use of the anti-S100A8 or the composition described herein for stimulating cell differentiation.

It is also provided the use of the anti-S100A8 or the composition described herein for inhibiting cell proliferation.

In an embodiment, the subject is a mammal.

In another embodiment, the subject is a mouse or a human.

In an embodiment, the composition described herein further comprises a S100A9 peptide or a peptidomimetic thereof.

In another embodiment, the anti-S100A8 encompassed herein is formulated for an administration with an S100A9 peptide.

In another embodiment, the S100A9 peptide is human S100A9 protein.

In a further embodiment, wherein the peptide comprises the amino acid sequence set forth in SEQ ID NO: 7.

In an additional embodiment, the peptide has at least 60%, at least 70% or at least 80%, at least 90% identical, or at least about 95% identity with SEQ ID NO: 7.

In another embodiment, the peptide consists of the amino acid sequence set forth in SEQ ID NO: 7.

BRIEF DESCRIPTION OF THE DRAWINGS

Reference will now be made to the accompanying drawings.

DETAILED DESCRIPTION

Figure 1:
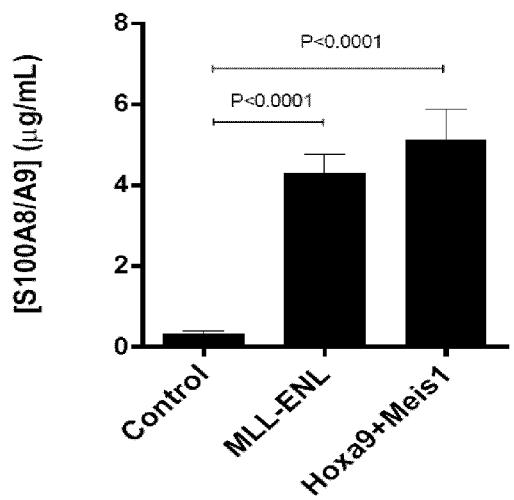
FIG. 1 illustrates the secretion of S100A8/A9 in the serum of mice with primary leukemia, wherein primary leukemia were generated by injecting mouse hematopoietic stem/progenitor cells transfected with a retrovirus expressing GFP, as well as the genes HOXA9 and MEIS1 or the fusion gene MLL-ENL, the S100A8/A9 concentrations measured by ELISA in serum (data are the mean±sem of 3 independent measurements).

It is provided an anti-S100A8 for treating or preventing leukemia.

Accordingly, it is described herein the use of anti-S100A8 being an antibody for treating or preventing leukemia.

Leukemia encompassed herein can be acute lymphoblastic leukemia (ALL), acute myeloid leukemia (AML), chronic lymphocytic leukemia (CLL) chronic myeloid leukemia (CML) and/or chronic myelomonocytic leukemia (CMML).

The S100 protein family comprises 22 members of small (10 to 14 kDa) acidic calcium-binding proteins named as S100A1, S100A2, and so on, according to the time of their discovery and on the chromosome on which they are found. These intracellular proteins are involved in the control of protein phosphorylation, enzymatic activities, $Ca^{2+}$ homeostasis, and intermediate filaments polymerisation. S100A8, S100A9 and S100A12 belong to a subset called myeloid related proteins (MRPs) because they are predominantly expressed in neutrophils (30% of cytoplasmic protein) and monocytes, which derive from myeloid precursors.

S100A8 and S100A9 are arranged as noncovalently bonded homodimers. In addition, in the presence of calcium, S100A8 and S100A9 form a noncovalent heterodimer called S100A8/A9 or calprotectin, presumed to be involved in the cellular control of calcium concentrations.

S100A8 and S100A9 are arranged as non-covalently bonded homodimers. S100A8 and S100A9 also form a noncovalent heterodimer called S100A8/A9 or calprotectin in presence of calcium, and this heterodimer is presumed to be involved in the cellular control of calcium concentrations. Inside the cells, calprotectin binds to lipids and activates NADPH oxidase inside neutrophils, at least in part by transferring arachidonic acid to NADPH oxidase. S100A8 and S100A9 are presumed to bind to RAGE, the scavenger receptor (CD36) or the Toll-like receptor 4 (TLR4).

Human peptide sequence of S100A8 consists of:

```
                                        (SEQ ID NO: 1)
MLTELEKALNSIIDVYHKYSLIKGNFHAVYRDDLKKLLETECPQYIRKKG
ADVWFKELDINTDGAVNFQEFLILVIKMGVAAHKKSHEESHKE.
```

Accordingly it is disclosed humanized antibodies and antibodies from non-human species against S100A8, and particularly human S100A8, whose protein sequences can be modified to increase their similarity to antibody variants produced naturally in humans. Humanization can be necessary when the process of developing a specific antibody involves generation in a non-human immune system (such as that in mice). Antibody humanization methods are designed to produce a molecule with minimal immunogenicity when applied to humans, while retaining the specificity and affinity of the parental non-human antibody. The protein sequences of antibodies produced in this way are partially distinct from homologous antibodies occurring naturally in humans, and are therefore potentially immunogenic when administered to human patients.

Humanized antibodies encompassed herein can be produced via enrichment technologies such as phage display or immunization of transgenic mice bearing the antibody human gene repertoire have provided powerful means to generate human antibodies.

More particularly, the antibody described herein specifically binds to an epitope on S100A8.

In a particular embodiment, the antibody comprises an epitope binding fragment that is selected from: Fv and/or F(ab') and/or F(ab')2. In particular, the antibody comprises an epitope-binding single chain antibody.

Particularly, the antibody encompassed herein comprises a heavy chain variable region encoded by nucleotide sequence:

```
                                        (SEQ ID NO: 3)
GGATCCCAGGTTCAGCTGCAGCAGTCAGGGGCAGAGCTTGTGAAGCCAGG

GGCCTCAGTCAAGTTGTCCTGCACAGCTTCTGGCTTCAACATTAAAGACA

CCTATTTGCACTGGGTGAAGCAGAGGCCTGAGCAGGGCCTGGAGTGGGTT

GGAAGGATTGATCCTGCGAATGGTGATACTAAATATGACCCGAAGTTCCA

GGCCAAGGCCACTATAACAGCTGACACAACCTCCAACACAGCCTACGTGC

ACCTCAACAGCCTGACATCTGAGGACACTGCCGTCTATTTCTGTACTGGG

GGATGGCAGATGGGGGGCCGGTACTTCGATGTCTGGGGCGCAGGGACAAC

GGTCACCGTCTCCTCAGCCAAAACGACACCCCCATCTGTCTATGGTGGCG

GTGGTTCT.
```

In a particular embodiment, the antibody comprises a heavy chain variable region consisting of:

```
                                        (SEQ ID NO: 4)
GSQVQLQQSGAELVKPGASVKLSCTASGFNIKDTYLHWVKQRPEQGLEW
VGRIDPANGDTKYDPKFQAKATITADTTSNTAYVHLNSLTSEDTAVYFC
TGGWQMGGRYFDVWGAGTTVTVSSAKTTPPSVYGGGGS.
```

Particularly, the antibody encompassed herein comprises a light chain variable region encoded by nucleotide sequence:

```
                                        (SEQ ID NO: 5)
GATGTTGTGATGACCCAGTCTCCTGCTTCCTTAGCTGTATCTCTGGGGC

AGAGGGCCACCATCTCATACAGGGCCAGCAAAAGTGTCAGTACATCTGG

CTATAGTTATATGCACTGGAACCAACAGAAACCAGGACAGCCACCCAGA

CTCCTCATCTATCTTGTATCCAACCTAGAATCTGGGGTCCCTGCCAGGT

TCAGTGGCAGTGGGTCTGGGACAGACTTCACCCTCAACATCCATCCTGT

GGAGGAGGAGGATGCTGCAACCTATTACTGTCAGCACATTAGGGAGCTT

ACACGTTCGGAGGGGGGACCAAGCTGGAAATAA.
```

In a particular embodiment, the antibody comprises a light chain variable region consisting of:

```
                                        (SEQ ID NO: 6)
DVVMTQSPASLAVSLGQRATISYRASKSVSTSGYSYMHWNQQKPGQPPR
LLIYLVSNLESGVPARFSGSGSGTDFTLNIHPVEEEDAATYYCQHIREL
TRSEGGPSWK.
```

The anti-S100 Ab described herein may be employed in admixture with a suitable physiological or pharmaceutical carrier. Such compositions comprise a therapeutically effective amount of the antibody, and a physiologically or a pharmaceutically acceptable carrier or excipient. Such a carrier includes but is not limited to saline, buffered saline, dextrose, water, glycerol, ethanol, and combinations thereof. The formulation should suit the mode of administration.

An antibody as defined herein, acting as inhibitor or antagonist of S100A8 protein, can be administered alone or in combination with other antibodies directed toward other complementary targets, including but not limited to, other S100 polynucleotides or polypeptides.

The antibodies encompassed herein may be advantageously utilized in combination with other monoclonal or chimeric antibodies, with cytokines, or with S100 proteins. The antibodies may be administered alone or in combination with other types of treatments. For example, the antibody described herein can be administered in combination, simultaneously or separately, with for example a chemotherapeutic agent, such as daunorubicin (Cerubidine), doxorubicin (Adriamycin), and cytarabine. Generally, administration of products of a species origin or species reactivity (in the case of antibodies) that is the same species as that of the patient is preferred. Thus, in a preferred embodiment, human antibodies, fragments, derivatives, or analogs are administered to a human or animal patient for therapy or prophylaxis.

It is preferred to use high affinity and/or potent in vivo inhibiting and/or neutralizing antibodies against S100 polypeptides or polynucleotides encompassed herein, fragments or regions thereof, for therapy of disorders related to S100 polynucleotides or polypeptides, including fragments thereof. Such antibodies, fragments, or regions, will preferably have an affinity for S100 polypeptide encompassed herein.

Particularly, there is provided a method for treating leukemia comprising the step of administering to a subject in need thereof an effective amount of the antibody as defined herein or the composition as defined herein.

The Cancer Genome Atlas (TCGA) Research Network performed whole genome/whole exome sequencing on 200 adult AML cases along with RNA, microRNA and DNA-methylation analysis. S100A8 and S100A9 were amongst the top 5 discriminatory genes for one important sub-group mainly composed of myelomonocytic and monocytic AML, with high RPKM levels (Cancer Genome Atlas Research, N., 2013, The New England journal of medicine, 368: 2059-2074). High concentrations of S100A8 and S100A9 proteins are found in the serum of patients with acute and chronic myeloid leukemia (Ivanov et al., 1996, Immunology letters, 49: 7-13), and these concentrations correlate with growth-stimulating activity in these sera. In addition, S100A8 has been identified as a predictor of poor survival in de novo AML patients (Nicolas et al., 2011, Leukemia: official journal of the Leukemia Society of America, Leukemia Research Fund, U.K, 25: 57-65). Constitutive overexpression of S100A8/A9 is also associated with resistance to prednisone treatment in MLL-rearranged B-ALL, and forced expression of S100A8/A9 in MLL-rearranged B-ALL cells transform prednisone-sensitive into prednisone insensitive in vitro (Spijkers-Hagelstein et al., 2012, Leukemia: official journal of the Leukemia Society of America, Leukemia Research Fund, U.K, 26: 1255-1265).

Figure 2:
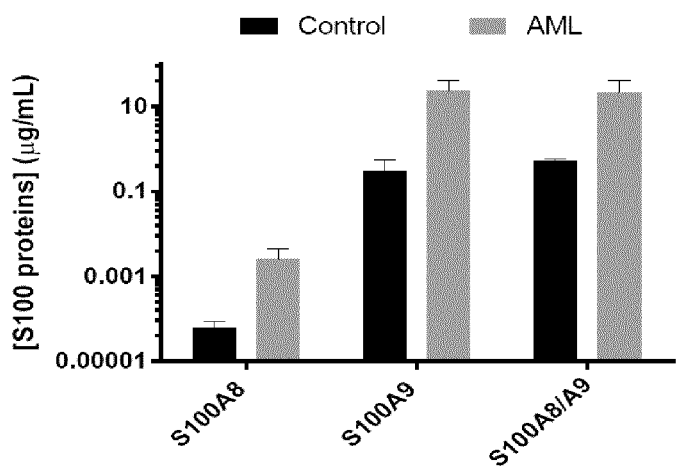
FIG. 2 illustrates the level of S100A8, S100A9, and S100A8/A9 secreted in the serum of mice with primary leukemia, wherein primary leukemia were generated by injecting mouse hematopoietic stem/progenitor cells transfected with a retrovirus expressing GFP, as well as the genes HOXA9 and MEIS1, secondary leukemia then induced by injecting 100,000 bone marrow cells from a leukemic mouse to controlled mice, and the S100A8/A9 concentrations measured by ELISA in serum (data are the mean±sem of 3 independent measurements).
Figure 3:
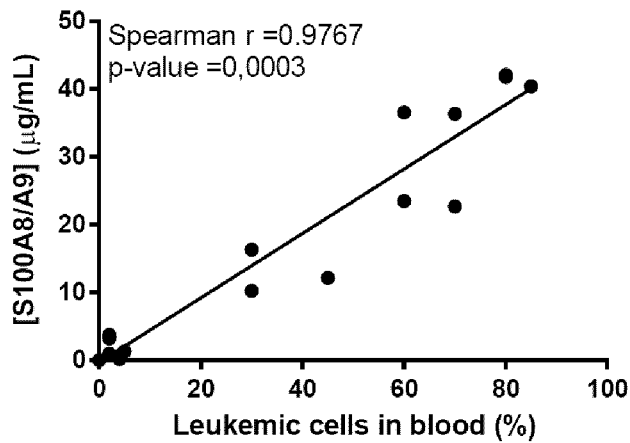
FIG. 3 illustrates the correlation between the secretion of S100A8/A9 and the presence of leukemia cells in the peripheral blood, wherein primary leukemia were generated by injecting mouse hematopoietic stem/progenitor cells transfected with a retrovirus expressing GFP, as well as the genes HOXA9 and MEIS1, secondary leukemia then induced by injecting 100,000 bone marrow cells from a leukemic mouse to naïve mice, and the number of leukemic cells in the blood was determined by flow cytometry, S100A8/A9 concentrations measured by ELISA in serum (data are the mean±sem of 3 independent measurements).

To address the possible involvement of S100A8 and S100A9 proteins in AML, their expression was measured using two well-characterized myeloid leukemia models induced by overexpression of Hoxa9 and the cofactor Meis1 or expression of the oncogene MLL-ENL in hematopoietic progenitors and stem cells (HPSC) transplanted into lethally irradiated recipient. As in AML patients, it was observed a substantial increase of S100A8/A9 concentration in plasma of primary recipient mice expressing Hoxa9 and Meis1 (H9M) and MLL-ENL (5.0 µg/mL±1.0 µg/mL and 3.8 µg/mL±0.5 µg/mL, respectively) compared to control mice (0.5 µg/mL±0.08 µg/mL) (see FIG. 1). S100A8/A9 levels in plasma of H9M secondary recipient was also increased by an approximatively tenfold. Although the heterodimeric form was predominant, both homodimeric S100A8 and S100A9 were observed in plasma of AML mice (see FIG. 2). Elevated concentrations of S100A8/A9 were found in bone marrow and spleen supernatants of AML recipient, indicating that extracellular fluids are also enriched in those proteins. S100A8/A9 concentration gradually increased as leukemia progressed and strongly correlated to regress of leukemic cells from the bone marrow to the blood (see FIG. 3).

Figure 4:
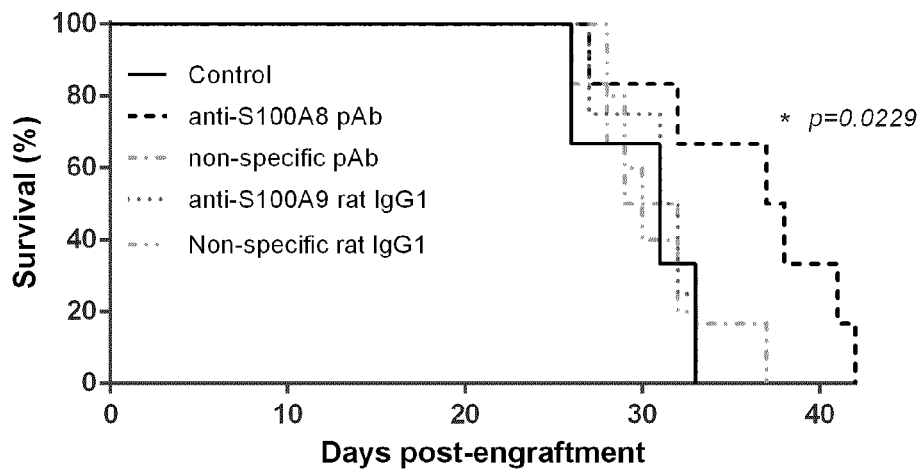
FIG. 4 illustrates that an anti-S100A8 antibody in accordance to one embodiment prolong survival of secondary mice injected with HOXA9-MEIS1 leukemia, wherein 100,000 bone marrow cells from a HOXA9-MEIS1 primary leukemic mouse were injected 3 times a week from day 3 till day 35 in sub-lethally irradiated secondary mice with rabbit anti-S100A8 pAbs or non-specific rabbit IgGs (150 µg/injection), rat anti-S100A9 mAb or isotype control Ab (rat IgG1) or PBS (control) (6 mice per group).
Figure 5:
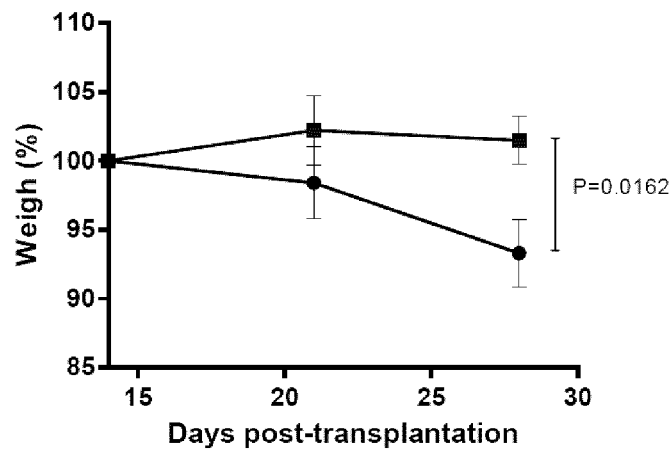
FIG. 5 illustrates that an anti-S100A8 antibody in accordance to one embodiment reduces weight loss of secondary mice injected with HOXA9-MEIS1 leukemia, wherein 100,000 bone marrow cells from a HOXA9-MEIS1 primary leukemic mouse were injected 3 times a week from day 3 till day 35 in sub-lethally irradiated secondary mice with rabbit anti-S100A8 pAbs or non-specific rabbit IgGs (150 µg/injection) (6 mice per group).
Figure 6:
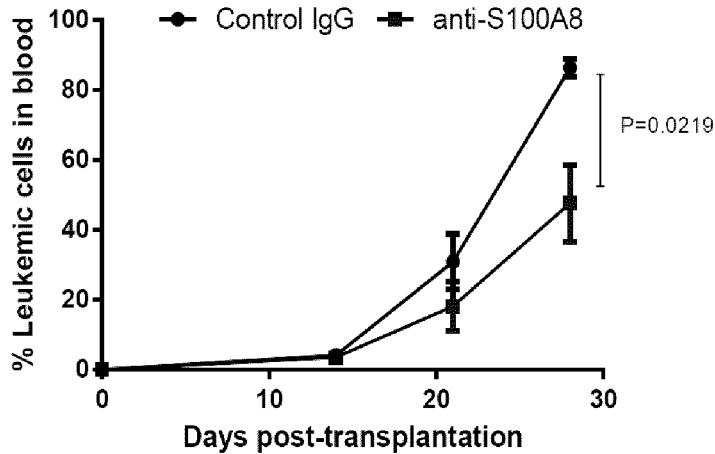
FIG. 6 illustrates that an anti-S100A8 antibody in accordance to one embodiment delays the appearance of leukemic cells in the peripheral blood, wherein 100,000 bone marrow cells from a HOXA9-MEIS1 primary leukemic mouse were injected 3 times a week from day 3 till day 35 in sub-lethally irradiated secondary mice with rabbit anti-S100A8 pAbs or non-specific rabbit IgGs (150 µg/injection) (6 mice per group), the number of leukemia cells determined by flow cytometry.
Figure 7:
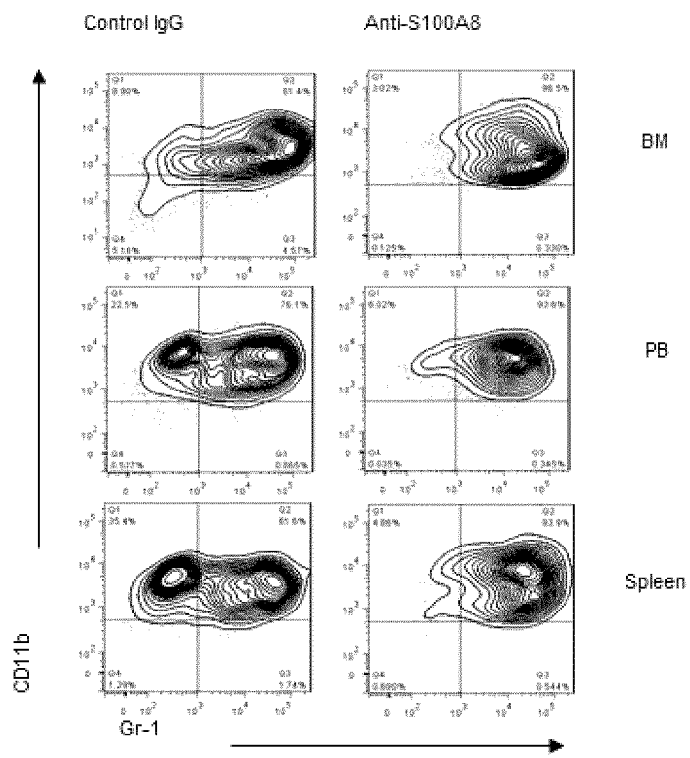
FIG. 7 illustrates that an anti-S100A8 antibody in accordance to one embodiment increases differentiation of AML blast cells, wherein 100,000 bone marrow cells from a HOXA9-MEIS1 primary leukemic mouse were injected 3 times a week from day 3 till day 35 in sub-lethally irradiated secondary mice with rabbit anti-S100A8 pAbs or non-specific rabbit IgGs (150 µg/injection) (6 mice per group), and wherein moribund mice were sacrificed, peripheral blood, spleen, and bone marrow were harvested and the cells were analyzed by flow cytometry for the expression of differentiation markers (CD11b and Gr1) (data are from one mouse representative of 3 others).
Figure 8:
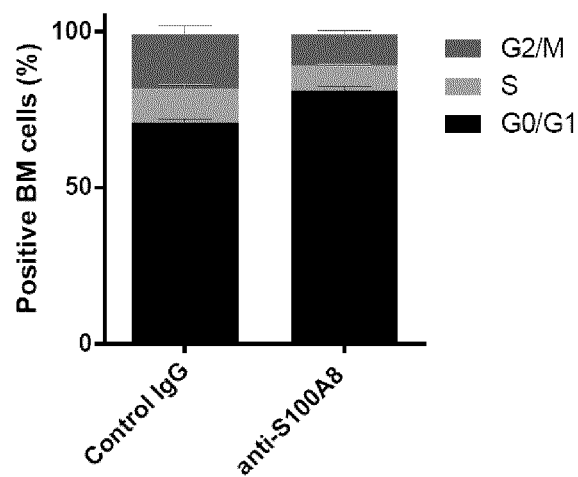
FIG. 8 illustrates that an anti-S100A8 antibody in accordance to one embodiment inhibits proliferation of AML blast cells, wherein 100,000 bone marrow cells from a HOXA9-MEIS1 primary leukemic mouse were injected 3 times a week from day 3 till day 35 in sub-lethally irradiated secondary mice with rabbit anti-S100A8 pAbs or non-specific rabbit IgGs (150 µg/injection) (6 mice per group), wherein moribund mice were sacrificed and bone marrow were harvested, and cell cycle was analyzed by propidium iodide staining (data are the mean of 3 experiments).
Figure 9:
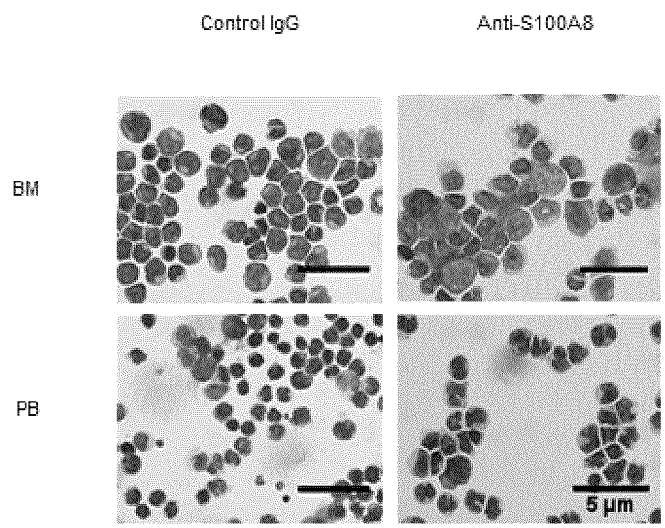
FIG. 9 illustrates the increased differentiation of AML cells in anti-S100A8-treated mice, wherein 100,000 bone marrow cells from a HOXA9-MEIS1 primary leukemic mouse were injected 3 times a week from day 3 till day 35 in sub-lethally irradiated secondary mice with rabbit anti-S100A8 pAbs or non-specific rabbit IgGs (150 µg/injection) (6 mice per group), wherein moribund mice were sacrificed, peripheral blood and bone marrow were harvested, the cells were then stained with Wright-Giemsa to reveal cellular morphology (data are from one mouse representative of 3 others).

To investigate the roles of S100A8 and S100A9 in leukemia progression, H9M driven AML secondary recipients were treated i.p with 10 mg/kg of either pAb anti-S100A8 or with mAb anti-S100A9. These antibodies interact with both homodimeric S100A8/A8 or S100A9/A9 respectively, and heterodimeric S100A8/A9. Injection of anti-S100A8 led to a marked delay in leukemia progression and significantly extended survival compared to control immunoglobulins (FIG. 4). This was associated with reduced weight loss and improvement of the behavior of leukemic mice in anti-S100A8-treated mice (FIG. 5). The percentage of leukemic cells in peripheral blood of anti-S100A8 treated mice and S100A8/A9 concentrations were also significantly reduced (FIG. 6). In contrast, no difference was observed between control IgG and anti-S100A9-treated mice in terms of plasma S100A8/A9 levels, leukemic cells in blood or overall survival (FIG. 4). Analysis of anti-S100A8 treated mice revealed an increase of mature myeloid cell marker CD11b and Gr1 expression (FIG. 7), cells in G0/G1 cell cycle phases (FIG. 8) and cytological modifications characteristic of granulocytic cells (FIG. 9) whereas no changes were observed in anti-S100A9 suggesting enhancement of AML cell differentiation and that the anti-S100A8 had induced myeloid differentiation. Accordingly, S100A8 promotes AML pathogenesis by interfering with myeloid cell differentiation.

Figure 10:
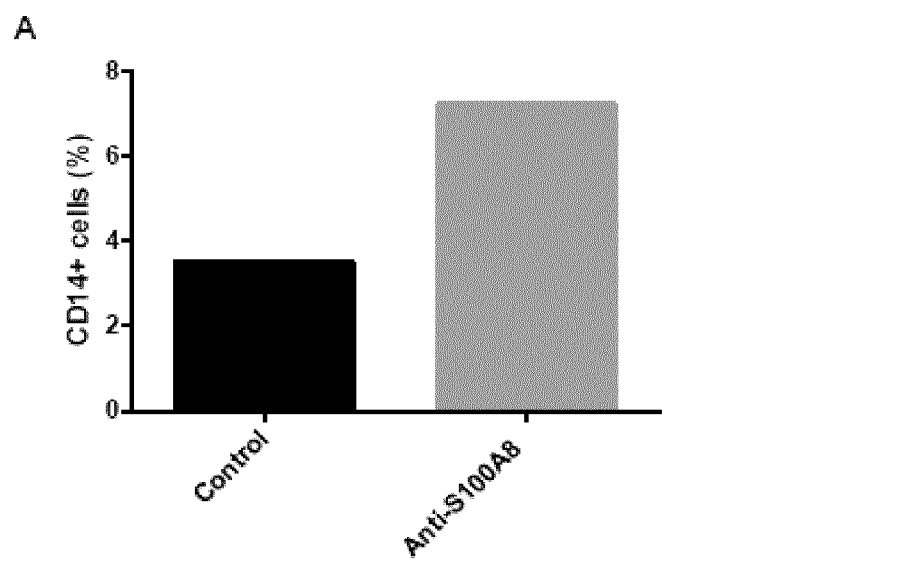
FIG. 10 illustrates that an anti-S100A8 antibody in accordance to one embodiment promotes the differentiation and growth arrest of human leukemia cells, wherein human cord blood cells expressing the fusion gene MLL-AF9 were stimulated with anti-S100A8 mAb 1F8 (20 µg/ml) or an isotype control Ab for 72 h, showing in (A) the cells labelled with anti-CD14 and examined by flow cytometry; and in (B) cell cycle analyzed by propidium iodide staining.
Figure 10:
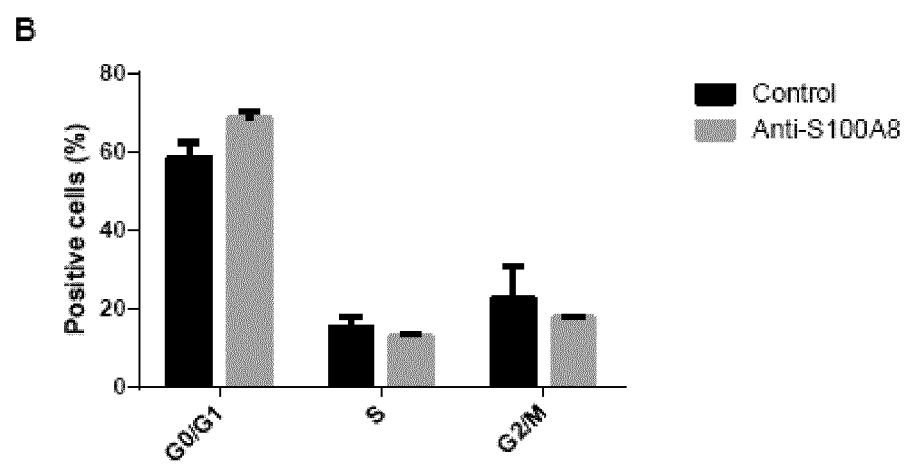

To confirm the effect of the anti-S100A8, human cord blood cells transfected with the fusion gene MLL-AF9 were stimulated with anti-S100A8 for 72 h. Cell differentiation was examined using expression of CD14 as a marker of cell differentiation. Anti-S100A8 mAb 1F8 doubled the number of cells expressing of CD14 (FIG. 10A), suggesting a stimulation of cell differentiation. In addition, anti-S100A8 mAb 1F8 increased the number of cells in G0/G1 and S phases (FIG. 10B), indicating an inhibition of proliferation of the cells.

Figure 11:
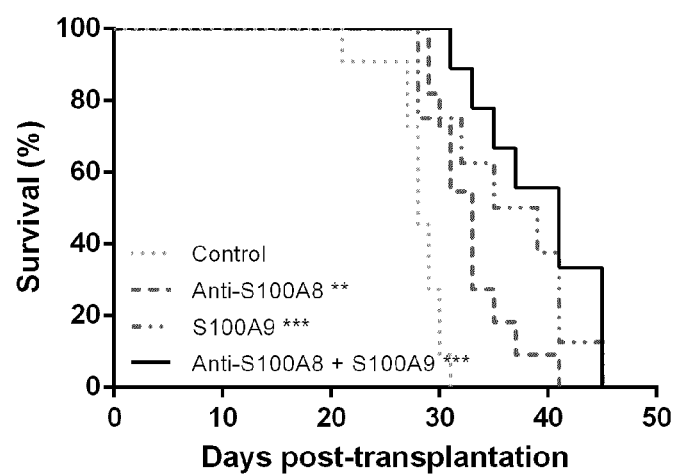
FIG. 11 illustrates that an anti-S100A8 antibody in combination with a S100A9 peptide in accordance to one embodiment prolong survival of secondary mice injected with HOXA9-MEIS1 leukemia, wherein bone marrow cells from a HOXA9-MEIS1 primary leukemic mouse were injected in sub-lethally irradiated secondary mice with anti-S100A8, S100A9 peptide or a combination thereof.

As shown in FIG. 11, the anti-S100A8 antibody encompassed herein can be administered with a S100A9 peptide in order to significantly increase the delay in leukemia progression and extended survival compared to control immunoglobulins or compared to administration of the anti-S100A8 antibody or S100A9 peptide alone.

S100A9, also known as calgranulin B and myeloid related protein-14 (MRP-14), is a calcium- and zinc-binding protein that belongs to the S100 protein family. S100A9 is highly expressed by the myeloid cell lineage and is found in the extracellular milieu during inflammatory conditions. S100A9 forms heterodimers with S100A8, another member of the S100 family. However, S100A9 may also form monomers which execute specific functions. Human S100A9 has a molecular mass of about 13 kDa and is composed of 114 amino acid residues.

```
Human S100A9
                                         (SEQ ID NO: 7)
         10         20         30         40
    MTCKMSQLER NIETIINTFH QYSVKLGHPD TLNQGEFKEL 50         60         70         80
    VRKDLQNFLK KENKNEKVIE HIMEDLDTNA DKQLSFEEFI 90        100        110
    MLMARLTWAS HEKMHEGDEG PGHHHKPGLG EGTP
```

Accordingly, it is disclosed a composition comprising an anti-S100A8 antibody and a S100A9 peptide.

More particularly, it is disclosed a composition comprising an anti-S100A8 antibody comprising a heavy chain variable region encoded by the nucleotide sequence set forth in SEQ ID NO: 3 or 4, a light chain variable region encoded by the nucleotide sequence set forth in SEQ ID NO: 5 or 6, and a S100A9 peptide comprising the amino acid sequence set forth in SEQ ID NO: 7 for treating leukemia.

Accordingly, injection of anti-S100A8 protects from AML by promoting the differentiation of leukemia cells, resulting in reduced proliferation.

The present disclosure will be more readily understood by referring to the following examples which are given to illustrate embodiments rather than to limit its scope.

Example I

Bone Marrow Progenitor Cell Transduction and Transplantation Procedure

Bone marrow cells isolated from 5-fluorouracyl-treated C57BL/6 mice (8-12 week old female) were cultivated 2 days in DMEM with 15% fetal calf serum with 10 ng/ml IL-3, 10 ng/ml IL-6 and 100 ng/ml stem cell factor to promote cell cycle entry. Bone marrow cells were then co-cultured with irradiated GP+E86 cells transfected with MSCV-hoxa9-ires-meis1 hpgk-EGFP (virus producing cells) in presence of 5 µg/ml of polybrene for 2 days.

Primary leukemia recipient C57BL/6 mice were irradiated (7 Gy), then injected i.v. 24 h later with $4 \times 10^5$ infected bone marrow cells (expressing Hoxa9, Meis1 and Egfp). Mice were followed every day for signs of leukemia. Peripheral blood was harvested every week to quantify the number of leukemia cells (expressing GFP) by flow cytometry. Moribund mice were sacrificed and the peripheral blood and bone marrow were harvested.

Secondary leukemia were induced by injecting $2 \times 10^5$ bone marrow cells from primary leukemia mice into sublethally irradiated (4Gy) recipient.

Example II

Anti-S100A8 Antibody Treatment

Leukemic cells isolated from bone marrow of primary leukemia mice were injected into sublethally irradiated (4Gy) recipient C57BL/6 mice. The presence of AML cells (EGFP+) in peripheral blood was evaluated by flow cytometry 14 days later. Mice were injected i.p three times per week with 100 µg purified rabbit IgG anti-S100A8 starting on day 3. Mice exhibiting signs of ill health were sacrificed and peripheral blood and bone marrow were harvested for histology and flow cytometry analyses.

Example III

Stimulation MLL-AF9

Human cord blood cells transfected with the fusion gene MLL-AF9 were cultivated in IMDM supplemented with 15% fetal calf serum, IL-6 and stem cell factor. The cells were plated 96 well microtiter plates (200 000 cells/well), then stimulated with 20 µg/ml of mAb 1F8 anti-S100A8, or PBS. After 72 h, cells were collected and immunophenotyping was performed by flow cytometry following staining with anti-CD14. Cell cycle was analyzed by propidium iodide staining.

Example IV

Combination of Anti-S100A8 and S100A9 Peptide

Leukemic cells isolated from bone marrow of primary leukemia mice were injected into sublethally irradiated (4Gy) recipient C57BL/6 mice. The presence of AML cells (EGFP+) in peripheral blood was evaluated by flow cytometry 14 days later. Mice were injected i.p three times per week with 100 µg purified rabbit IgG anti-S100A8, 20 µg of recombinant mouse S100A9 protein, or a combination of anti-S100A8 and S100A9 protein starting on day 3. Mice exhibiting signs of ill health were sacrificed and peripheral blood and bone marrow were harvested for histology and flow cytometry analyses.

While the disclosure has been described in connection with specific embodiments thereof, it will be understood that it is capable of further modifications and this application is intended to cover any variations, uses, or adaptations following, including such departures from the present disclosure as come within known or customary practice within the art to which the disclosure pertains and as may be applied to the essential features hereinbefore set forth, and as follows in the scope of the appended claims.

What is claimed is:

1. An anti-S100A8 antibody, wherein said anti-S100A8 antibody comprises a heavy chain variable region encoded by the nucleotide sequence set forth in SEQ ID NO: 3 or a heavy chain variable region consisting of SEQ ID NO: 4, and said anti-S100A8 antibody comprises a light chain variable region encoded by the nucleotide sequence set forth in SEQ ID NO: 5 or a light chain variable region consisting of SEQ ID NO: 6.

2. The anti-S100A8 antibody of claim 1, wherein said anti-S100A8 specifically binds to a S100A8/S100A8 homodimer or a S100A8/S100A9 heterodimer.

3. The anti-S100A8 antibody of claim 2, wherein the anti-S100A8 specifically binds to S100A8 protein is a human S100A8.

4. The anti-S100A8 antibody of claim 3, wherein the human S100A8 comprises the amino acid sequence depicted in SEQ ID NO: 1.

5. The anti-S100A8 antibody of claim 1, wherein said anti-S100A8 is monoclonal or polyclonal antibody.

6. The anti-S100A8 antibody of claim 1, wherein said anti-S100A8 is a mouse antibody, a goat antibody, a human antibody or a rabbit antibody.

7. The anti-S100A8 antibody of claim 1, wherein said anti-S100A8 is a humanized antibody.

8. The anti-S100A8 antibody claim 1, formulated for an administration with a chemotherapeutic agent.

9. The anti-S100A8 antibody of claim 8, wherein the chemotherapeutic agent is at least one of daunorubicin, doxorubicin and cytarabine.

10. A composition comprising the anti-S100A8 antibody claim 1 and a carrier.

11. The composition of claim 10, further comprising a S100A9 peptide or a peptidomimetic thereof.

12. The composition of claim 11, wherein the S100A9 peptide is human S100A9 protein.

13. A method of treating leukemia, stimulating cell differentiation, and/or for inhibiting cell proliferation in a subject comprising the step of administering the anti-S100A8 antibody claim 1 to said subject.

14. The method of claim 13, wherein said leukemia is acute lymphoblastic leukemia (ALL), acute myeloid leukemia (AML), chronic lymphocytic leukemia (CLL), chronic myeloid leukemia (CML) and chronic myelomonocytic leukemia (CMML).

* * * * *

SEQUENCE LISTING

<160> NUMBER OF SEQ ID NOS: 7

<210> SEQ ID NO 1
<211> LENGTH: 93
<212> TYPE: PRT
<213> ORGANISM: Human
<220> FEATURE:
<223> OTHER INFORMATION: S100A8

<400> SEQUENCE: 1

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
    50              55                  60

Ala Val Asn Phe Gln Glu Phe Leu Ile Leu Val Ile Lys Met Gly Val
65              70                  75                  80

Ala Ala His Lys Lys Ser His Glu Glu Ser His Lys Glu
                85                  90

<210> SEQ ID NO 2
<211> LENGTH: 279
<212> TYPE: DNA
<213> ORGANISM: Human
<220> FEATURE:
<223> OTHER INFORMATION: S100A8

<400> SEQUENCE: 2
atgttgaccg agctggagaa agccttgaac tctatcatcg acgtctacca caagtactcc      60
ctgataaagg ggaatttcca tgccgtctac agggatgacc tgaagaaatt gctagagacc     120
gagtgtcctc agtatatcag gaaaaagggt gcagacgtct ggttcaaaga gttggatatc     180
aacactgatg gtgcagttaa cttccaggag ttcctcattc tggtgataaa gatgggcgtg     240
gcagcccaca aaaaagcca tgaagaaagc cacaaagag                             279

<210> SEQ ID NO 3
<211> LENGTH: 408
<212> TYPE: DNA
<213> ORGANISM: Artificial Sequence
<220> FEATURE:
<223> OTHER INFORMATION: heavy chain variable region of anti-S100A8

<400> SEQUENCE: 3
ggatcccagg ttcagctgca gcagtcaggg gcagagcttg tgaagccagg ggcctcagtc      60
aagttgtcct gcacagcttc tggcttcaac attaaagaca cctatttgca ctgggtgaag     120
cagaggcctg agcagggcct ggagtgggtt ggaaggattg atcctgcgaa tggtgatact     180
aaatatgacc cgaagttcca ggccaaggcc actataacag ctgacacaac ctccaacaca     240
gcctacgtgc acctcaacag cctgacatct gaggacactg ccgtctattt ctgtactggg     300
ggatggcaga tgggggccg gtacttcgat gtctggggcg cagggacaac ggtcaccgtc     360
tcctcagcca aaacgacacc cccatctgtc tatggtggcg gtggttct                 408

<210> SEQ ID NO 4
<211> LENGTH: 136
<212> TYPE: PRT
<213> ORGANISM: Artificial Sequence
<220> FEATURE:
<223> OTHER INFORMATION: heavy chain variable region of anti-S100A8

<400> SEQUENCE: 4

Gly Ser Gln Val Gln Leu Gln Gln Ser Gly Ala Glu Leu Val Lys Pro
1               5                   10                  15

Gly Ala Ser Val Lys Leu Ser Cys Thr Ala Ser Gly Phe Asn Ile Lys
                20                  25                  30

Asp Thr Tyr Leu His Trp Val Lys Gln Arg Pro Glu Gln Gly Leu Glu
            35                  40                  45

Trp Val Gly Arg Ile Asp Pro Ala Asn Gly Asp Thr Lys Tyr Asp Pro
        50                  55                  60

Lys Phe Gln Ala Lys Ala Thr Ile Thr Ala Asp Thr Thr Ser Asn Thr
65                  70                  75                  80

```
Ala Tyr Val His Leu Asn Ser Leu Thr Ser Glu Asp Thr Ala Val Tyr
                85                  90                  95

Phe Cys Thr Gly Gly Trp Gln Met Gly Gly Arg Tyr Phe Asp Val Trp
            100                 105                 110

Gly Ala Gly Thr Thr Val Thr Val Ser Ser Ala Lys Thr Thr Pro Pro
        115                 120                 125

Ser Val Tyr Gly Gly Gly Ser
        130                 135

<210> SEQ ID NO 5
<211> LENGTH: 327
<212> TYPE: DNA
<213> ORGANISM: Artificial Sequence
<220> FEATURE:
<223> OTHER INFORMATION: light chain variable region of anti-S100A8

<400> SEQUENCE: 5
gatgttgtga tgacccagtc tcctgcttcc ttagctgtat ctctggggca gagggccacc      60
atctcataca gggccagcaa aagtgtcagt acatctggct atagttatat gcactggaac     120
caacagaaac caggacagcc acccagactc ctcatctatc ttgtatccaa cctagaatct     180
ggggtccctg ccaggttcag tggcagtggg tctgggacag acttcaccct caacatccat     240
cctgtggagg aggaggatgc tgcaacctat tactgtcagc acattaggga gcttacacgt     300
tcggaggggg gaccaagctg gaaataa                                         327

<210> SEQ ID NO 6
<211> LENGTH: 108
<212> TYPE: PRT
<213> ORGANISM: Artificial Sequence
<220> FEATURE:
<223> OTHER INFORMATION: light chain variable region of anti-S100A8

<400> SEQUENCE: 6

Asp Val Val Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Gly Gly Pro Ser Trp Lys
            100                 105

<210> SEQ ID NO 7
<211> LENGTH: 114
<212> TYPE: PRT
<213> ORGANISM: Human
<220> FEATURE:
<223> OTHER INFORMATION: S100A9
```

```
<400> SEQUENCE: 7

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
                20                  25                  30

Asn Gln Gly Glu Phe Lys Glu Leu Val Arg Lys Asp Leu Gln Asn Phe
            35                  40                  45

Leu Lys Lys Glu Asn Lys Asn Glu Lys Val Ile Glu His Ile Met Glu
        50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
                100             105                 110

Thr Pro
```